United States Patent [19]

Rosellini

[11] Patent Number: 5,143,414
[45] Date of Patent: Sep. 1, 1992

[54] MEDICAL DEVICE FOR HOLDING HYPODERMIC SYRINGE NEEDLE CAPS

[76] Inventor: Davey G. Rosellini, 1950 Balearic Dr., Costa Mesa, Calif. 92626

[21] Appl. No.: 587,069

[22] Filed: Sep. 24, 1990

[51] Int. Cl.⁵ .......................... A61M 5/32; B25B 9/00
[52] U.S. Cl. .................... 294/99.2; 128/919; 604/192; 604/263
[58] Field of Search .......... 294/99.2, 8.5, 11; 81/44; 128/919; 604/192, 198, 263

[56] References Cited

U.S. PATENT DOCUMENTS

| | | |
|---|---|---|
| 486,486 | 11/1892 | Lewis . |
| 656,492 | 8/1900 | Vogel . |
| 833,485 | 10/1906 | Rud . |
| 1,200,158 | 10/1916 | Barrett . |
| 1,368,446 | 2/1921 | Madsen . |
| 1,634,856 | 7/1927 | Skroch .................. 294/99.2 |
| 1,910,750 | 5/1933 | Clark . |
| 1,979,528 | 11/1934 | Bruce et al. ................ 219/8 |
| 2,124,039 | 7/1938 | Mitchell et al. ........... 254/23 |
| 2,876,778 | 3/1959 | Kees ...................... 128/346 |
| 2,903,078 | 9/1959 | Silenzi et al. ......... 294/99.2 X |
| 3,158,146 | 11/1964 | Handy ..................... 124/41 |
| 3,709,226 | 1/1973 | Santos ................... 128/340 |
| 4,165,745 | 8/1979 | Heifetz .................. 128/318 |
| 4,462,404 | 7/1984 | Schwarz et al. ......... 128/321 |
| 4,923,234 | 5/1990 | Fairley .................. 294/99.2 |
| 4,938,514 | 7/1990 | D'Addezio ............ 128/919 X |
| 4,950,015 | 8/1990 | Nejib et al. ............ 128/919 X |

FOREIGN PATENT DOCUMENTS 234421   5/1925   United Kingdom ............... 294/11

Primary Examiner—Margaret A. Focarino
Assistant Examiner—Dean J. Kramer
Attorney, Agent, or Firm—Walter A. Hackler

[57] ABSTRACT

A medical device for holding caps for capping hypodermic syringe needles includes an elongate, squeezeable handle, elongate first and second cap-holding jaws, the jaws being mounted to the handle so as to cause the jaws to be in a closed condition when the handle is not squeezed and so as to cause the jaws to open when the handle is squeezed. The jaws, which are formed of elongate halves of a tube, have an inner opening sized to grip a needle cap when the jaws are in the closed condition and have an axial length which is substantially greater than the cross sectional dimension of the inner opening when the jaws are closed. Distal edges of the jaws are made relatively thin so as to enable the jaws to pick up a needle cap from a surface when the handle is squeezed to open the jaws and squeezing pressure on the handle is then released. The handle includes a spring for urging the jaws toward the closed position when the handle is not squeezed. A stop is attached to one end of one of the jaws for preventing a held cap from being pushed axially through the jaws during a needle capping operation. The distal jaw edges may be formed having a plurality of teeth which interlock when the jaws are in the closed condition.

17 Claims, 2 Drawing Sheets

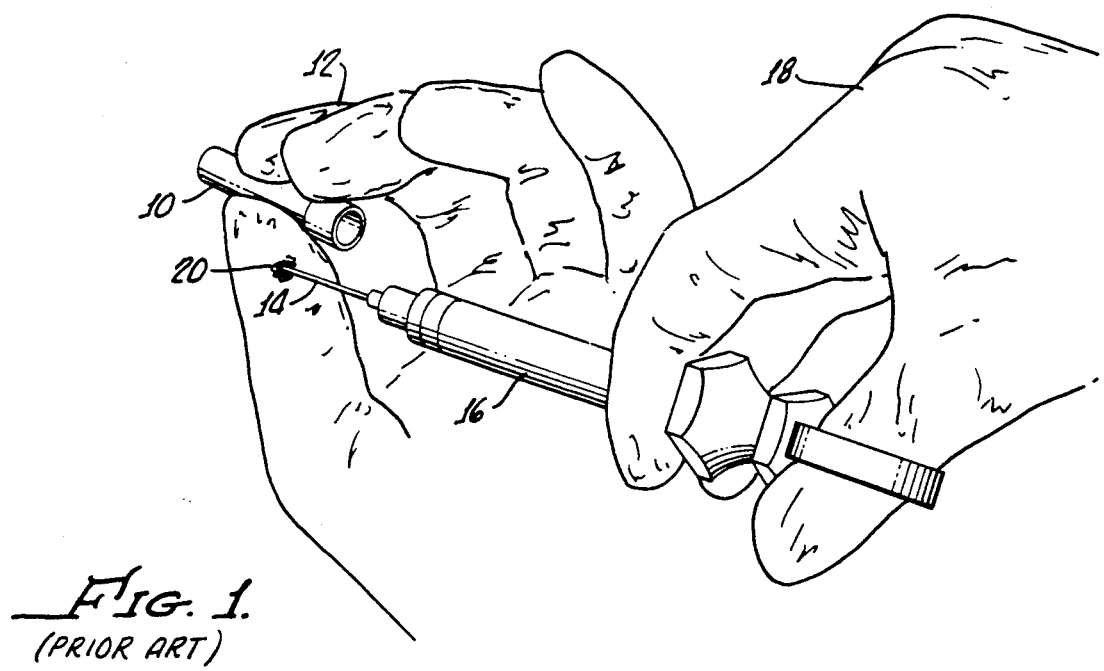
Fig. 1. (PRIOR ART)
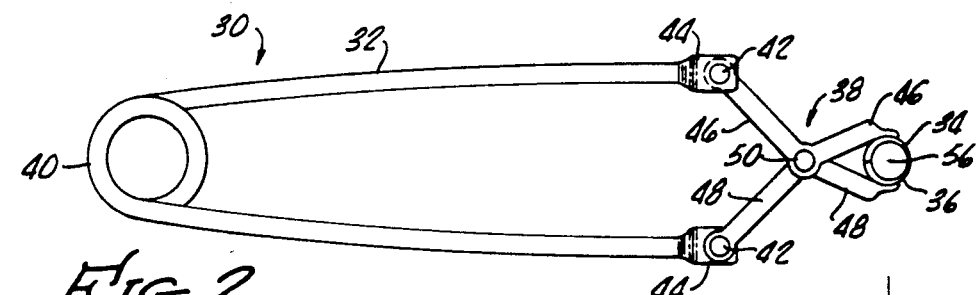
Fig. 2.
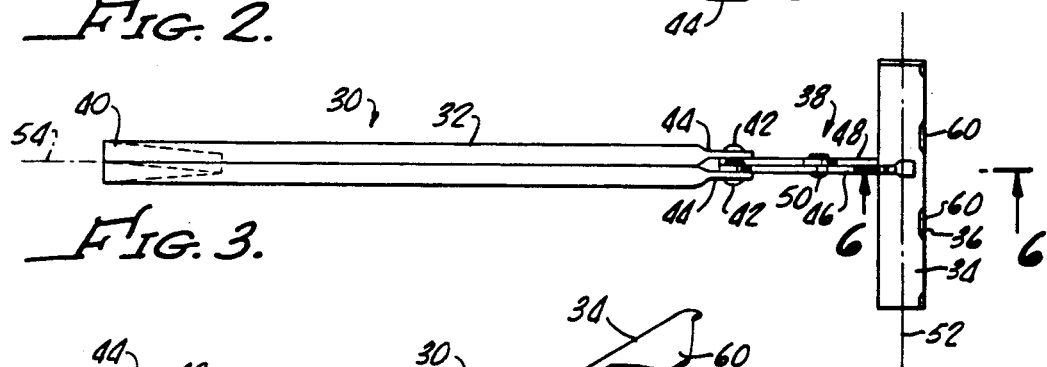
Fig. 3.
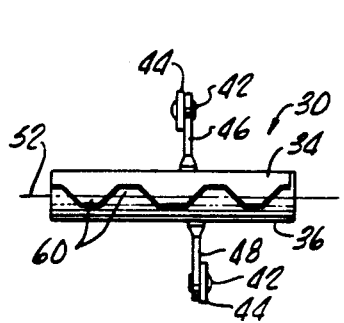
Fig. 4.
Fig. 5.

MEDICAL DEVICE FOR HOLDING HYPODERMIC SYRINGE NEEDLE CAPS

BACKGROUND OF THE INVENTION

1. Field of the invention

The present invention relates generally to the field of medical implements and, more particularly, to the field of medical implements configured for holding hypodermic syringe needle caps, especially while the needles are inserted into the caps or while the caps are installed over the needles so as to enable capping of the needles without having to hold the needle caps directly in one's hand.

2. Background Discussion

Most surgical procedures—both medical and dental—require the use of hypodermic syringes, either for the injecting of anesthetics, drugs, antibiotics, and/or other medical fluids into a patient's body or for the extraction of fluid samples from the patient's body. Hypodermic syringe needles need to be kept sterile prior to use and are, of necessity, extremely sharp. Consequently, such needles are commonly are provided with removable and replaceable needle caps which, when installed on the needles keep the needles sterile (or at least clean). Installed needle caps also protect users and handlers of the needles or hypodermic syringes on which the needles are installed, against accidental needlesticks. Thus, when syringe needles are being installed onto or removed from hypodermic syringes and when the syringes with needles installed are not in actual use, the capping of the needles is preferred for hygienic and safety reasons.

For many years bloodbourne diseases have been known to be transmittable from an infected individual to a non-infected individual by certain contact with the infected individual's blood, for example, if the infected individual's blood enters an open cut, sore or wound on the previously non-infected individual's body. Surgeons and other medical personnel who may contact a patient's or injured person's blood typically (except, perhaps, in cases of serious emergency) wear rubber surgical gloves which not only protect the patient or injured person against infection by germs and bacteria from the treating person's hands, but also protect the treating person from being infected, through cuts on the hands, from possibly being infected by the patient's or injured person's blood.

Needlesticks by hypodermic syringe needles used on patients (or other individuals) are another means whereby bloodbourne diseases can be transmitted from a patient to an individual treating the patient. In this regard, surgical gloves usually provide negligble protection for the wearers against accidental needlesticks.

Until a few years ago, the principal risk to healthcare professionals from accidental needlesticks was generally considered to be the contracting of hepatitis from an infected patient. As is well known Hepatitis B is still one of the major unresolved infectious disease problems of our time. It remains a threat to the public as well as to the health care community.

However, with the onset of AIDS (acquired imunodeficiency syndrome)—a fatal, bloodbourne disease for which no vaccination against nor cure for is presently known—a few years ago, the health risks associated with accidental needlesticks by used hypodermic syringe needles have escalated dramatically. In this regard, the sharing of hypodermic needles by users of controlled substances is well known to be a major factor in the rapid spread of AIDS. Thus, in spite of the great care exercised by healthcare professionals, accidental needlesticks by used hypodermic needles have been responsible for contracting AIDS. For example, in one widely-publicized case, a doctor reportedly contracted AIDS as a result of receiving a needlestick from an unseen and apparently improperly disposed hypodermic syringe needle. As another example, in a recent, reverse-twist case, a dental patient is believed to have contracted AIDS from a dentist who reportedly had AIDS, the theory (at least presently) being that the dentist may have experienced an accidental needlestick from the hypodermic syringe needle subsequently used to administer an anesthetic to the patient.

The risk of contracting or transmitting AIDS via accidental needlesticks presents healthcare professionals (as well as non-professionals, such as family members, who have to give injections, for example, insulin injections, to others) with a serious dilemma. On the one hand, the capping of hypodermic syringe needles whenever the associated syringe is not actually being used or when disposing of the needle (or entire syringe, as the case may be) is obviously highly desirable to prevent accidental needlesticks and the health risks associated therewith. Yet, on the other hand, the frequent capping and uncapping of hypodermic syringe needles increases the risk of accidental needlesticks for the individuals performing the capping operation. Moreover, the risk of an individual receiving an accidental needlestick during the needle recapping operation is greatly increased when the individual doing the recapping is physically or mentally distracted by other matters, such as the course of a medical treatment or operation and when the needle cap is held in one hand while the needle in inserted by the other hand into the cap (or while the manually-held cap is installed over the needle).

Many healthcare professionals have apparently concluded that the risks of receiving accidental needlesticks during needle recapping operations out weigh the risk of receiving an accidental needlestick from uncapped needles. In support of this conclusion, a current article on AIDS which appeared in a leading newspaper reported that many doctors, out of concern for contracting AIDS from accidental needlesticks, have opted for not recapping the hypodermic syringe needles they use.

Recognizing the very real concern of healthcare professionals regarding the present risks of accidental needlesticks, at least two types of holders for hypodermic syringe needle caps are known to have been advertised in trade journals. One such needle cap holder resembles the hilt portion of a sword in that it has a handle having a wide, disc-shaped protective handshield surrounding the cap receiving recess which extends downwardly into the handle. Accordingly is when the user inserts a hypodermic syringe needle into the cap he or she misses the cap opening with a needle, the needle merely hits the shield instead of the user's hand. The other advertised type of cap holder comprises a cylinder having a cap-receiving recess, the base of the cylinder being weighted so that the cylinder does not have to be held during the needle recapping operation. Alternatively, the base of the cylinder may be adhered to a surface, such as a table, tray or wall, by an adhesive strip on the base.

These advertised needle cap holders are too new for their efficacy or acceptance by healthcare professionals to have been determined. However, it appears that there may be difficulties associated with the sterilization, at least by commonly available means such as autoclaving, of such needle cap holders. In this regard, it can be appreciated that the cap holder can easily become contaminated by being handled by healthcare professionals whose gloved hands have come into contact with patients' body fluids (for example, blood and saliva), and from fluids on or discharged from the hypodermic syringe needles during the recapping operation. Moreover, any needle cap holder must be easy and convenient to use during surgical procedures or they simply will not be used. Furthermore, it goes without saying that the needle cap holders must substantially reduce the risk of accidental needlesticks during recapping operations—if the use of a cap holder is awkward and difficult to use, the risk of accidental needle sticks, perhaps in areas other than the users' hands, may be increased rather than decreased.

It is, therefore, a principal objective of the present invention to provide a hypodermic syringe needle cap holder which is convenient to use, requires no awkward movements, is of a familiar nature to healthcare professionals and is readily sterilized with commonly available sterilization methods and apparatus. Moreover, the present invention provides a needle cap holder which minimizes handling of the caps and which substantially reduces the risk of accidental needlesticks during the needle capping operation.

SUMMARY OF THE INVENTION

According to the present invention, there is provided a hypodermic syringe needle cap holder which is especially useful for the recapping of such needles, and which is preferably constructed of a medical grade of metal, such as stainless steel to permit sterilization by conventional autoclaving techniques. The needle cap holder comprises an elongate, manually-operable handle; first and second elongate cap-holding jaws which are preferably similar to one another and are constructed of elongate sections of tubing; and means for mounting the jaws to the handle so as to cause the jaws to be in a closed condition when the handle is not operated and so as to cause the jaws to open from the closed condition toward an open condition when the handle is operated by a user. The jaws have an inner opening sized to grip a needle cap when the jaws are in the closed condition and have an axial length which is substantially greater than the cross sectional dimension of the jaws when the jaws are in the closed condition.

The mounting means mount the jaws to the handle so that a longitudinal axis of the opening between the jaws is substantial perpendicular to the longitudinal axis of the handle and so that the jaws have one pair of longitudinally opposing edges which are distal relative to the handle and another pair of opposing longitudinal edges which are proximal relative to the handle. The pair of jaw distal edges are relatively thin so as to enable the jaws to pick up a needle cap from a surface when the handle is operated to cause the jaws to be in the open condition and when the jaws are then returned to the closed condition. The device preferably includes biasing means for urging the jaws toward the closed condition when the handle is not operated.

In accordance with a preferred embodiment of the invention, the device further includes stopping means attached to one end region of at least one of the jaws for preventing a held cap from being pushed axially through the jaws during a needle capping operation. Further in accordance with a preferred embodiment, the distal pair of opposing jaw edges are formed having a plurality of teeth which interlock when the jaws are in the closed condition.

Preferably the handle is configured so that the jaws are opened from the closed condition to the open condition by an operator squeezing on the handle. In such case, the jaw mounting means include motion multiplying means which enables the jaws to be opened relatively wide so that needle caps can be picked up through the distal edges of the jaws in response to relatively little squeezed movement of the handle.

Because of the manner in which the cap-holding device of the present invention is constructed, a hypodermic syringe needle cap can easily be picked up from a surface by squeezing the handle to open the jaws and placing the open jaws over the needle cap. Squeezing pressure on the handle is then released and the jaws automatically close over the needle cap which is then held by the device while the hypodermic syringe needle is inserted into the cap or while the cap is installed over the needle.

BRIEF DESCRIPTION OF THE DRAWINGS

The present invention can be more readily understood from a consideration of the following detailed description when taken with the accompanying drawings, in which:

FIG. 1 is a perspective drawing showing a typical manner in which a an accidental needlestick can result from attempting to insert a hypodermic syringe needle (installed on the syringe) into a needle cap held in one hand while the syringe is held in the other hand (this FIG. is labeled "PRIOR ART");

FIG. 2 is a plan view of a needle cap-holding device in accordance with the present invention, showing an elongate, spring-type handle and showing the attached needle cap-holding jaws in the closed, empty condition;

FIG. 3 is a side elevation view of the needle cap-holding device of FIG. 3, showing features of the cap-holding jaws;

FIG. 4 is a front elevation view of the needle cap-holding device of FIGS. 2 and 3, showing additional features of the cap-holding jaws;

FIG. 5 is a partial perspective drawing looking at the front of the needle cap-holding device showing the cap-holding jaws in a fully open condition;

Like elements and features in the various figures are given the same reference number or other identification.

DESCRIPTION OF THE PREFERRED EMBODIMENT

Figure 6:
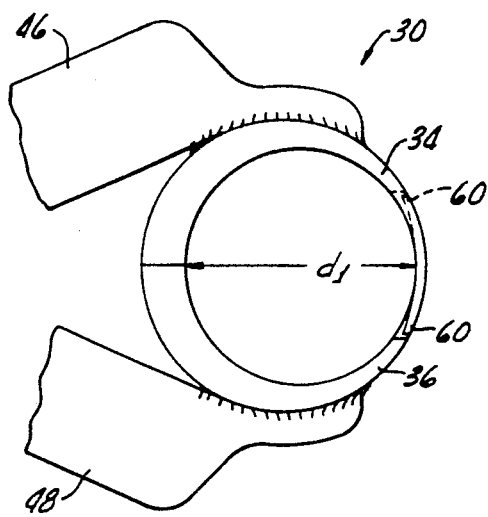
FIG. 6 is a transverse cross sectional view taken along line 6—6 of FIG. 3, showing the cap-holding jaws in the closed condition and showing thinned regions of the jaws along the distal, longitudinal edges thereof.

There is shown in FIG. 1 a typical manner in which a hypodermic needle cap 10 is manually held in one hand 12 of an individual while the individual tries to insert into cap 10 a needle 14 installed on an associated hypodermic syringe 16 held in the other hand 18 of the individual. FIG. 1 further shows how easy it has been for the individual performing the depicted needle capping operation to accidentally receive a needlestick 20 from needle 14 if the capping operation is not performed in an extremely careful manner.

To prevent, or at least to very substantially reduce, the risk of accidental needlesticks by needle 14 during the needle capping operation, a needle cap-holding device 30, according to the present invention, is provided, being particularly shown in FIGS. 2 though 6. As shown, cap-holding device 30 generally comprises an elongate, squeezeable handle 32; first and second cap-holding jaws 34 and 36, respectively; and jaw mounting means 38 which mount the pair of jaws to the handle As more particularly described below, jaw mounting means 38 comprise or include jaw movement multiplying means which cause jaws 34 and 36 to be opened widely in response to a relatively small squeezing of handle 32.

As seen from FIG. 2, handle 32 is formed of a stiff, spring-type rod which is bent through about 540 degrees at a coil spring end 40 thereof, the handle being formed into the general shape of an elongate "U," with the coil spring end 40 of the handle forming the bottom region of the "U." Pivotally attached, by pins 42 to otherwise free ends 44 of handle 32 are first ends of first and second jaw-mounting members 46 and 48, respectively. Each of members 46 and 48 are generally in the shape of an open "V," with the members being pivotally connected together in their central regions (that is, at the points of the "V"s) by a pivot pin 50 so that the two members are in the general shape of an "X."

Generally central longitudinal, outer surface regions of first and second jaws 34 and 36 are attached, for example, by welding, to second ends of respective first and second mounting members 46 and 48, as is best seen in FIGS. 2, 3, 4, 6 and 8. As can be seen in FIG. 3, and as is preferred but not necessary, jaws 34 and 36 are joined to ends of respective mounting members 46 and 48 so that a longitudinal axis 52 of the jaws is perpendicular to a longitudinal axis 54 of handle 32. Moreover, as shown in FIG. 4, and is also preferred but not required, jaws 34 and 36 are attached to mounting members 46 and 48 so that longitudinal axis 52 of the jaws is perpendicular to a plane through handle 32. It is considered by the present inventor that this orientation of jaws 34 and 36 relative to handle 32 enables cap-holding device 30 to be easy and natural to use.

Figure 8:
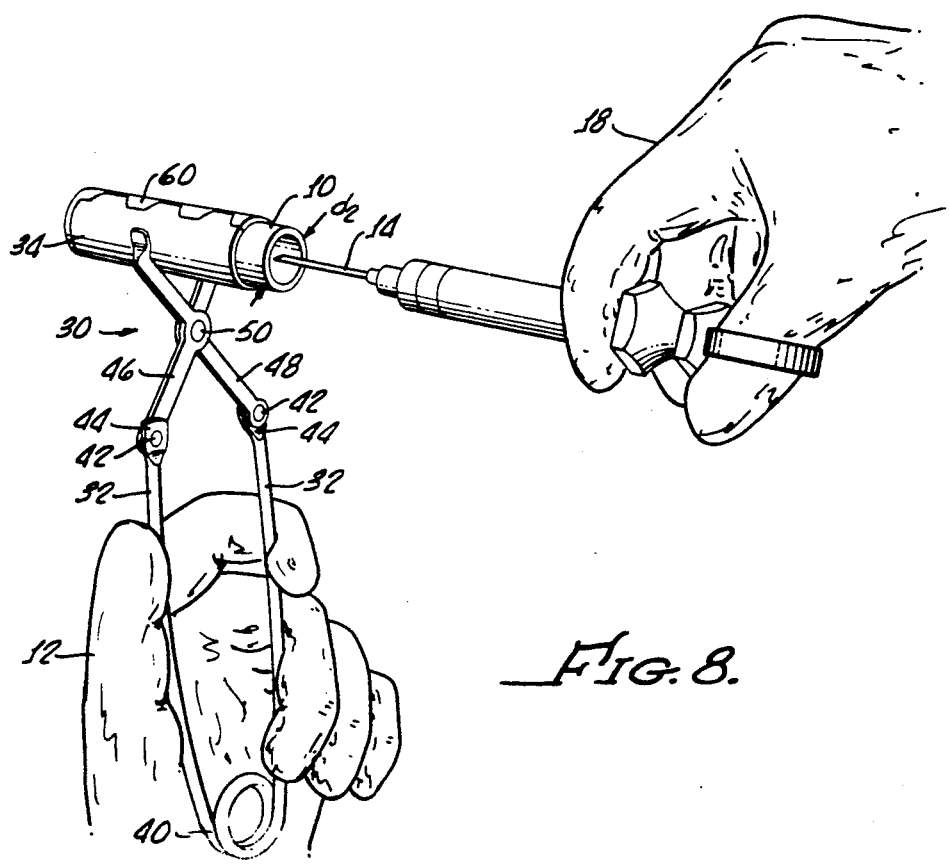
FIG. 8 is, a perspective drawing showing the manner in which a needle cap is held in the needle cap-holding device and showing the manner in which the hypodermic syringe needle is safely inserted into the held cap.

It is preferred for several reasons, including lightness in weight, ease of use and low cost of manufacture, that jaws 34 and 36 be constructed of a tubular shape and having a relatively thin wall. In some cases, jaws 34 and 36 are symmetrical in shape to one another and may be formed of split longitudinal halves or sections of an elongate tube. Jaws 34 and 36, when in the closed condition (FIG. 6), have an inner diameter, "$d_1$" which is somewhat less than the outside diameter "$d_2$" of needle cap 10 (FIG. 8), and have an axial length which is substantially greater than such inner diameter. Preferably the axial length of jaws 34 and 36 is only somewhat less than the length of needle cap 10. A disc-shaped stop 56 (FIG. 5) is attached, again as by welding, to one end of one of jaws 34 or 36, the attachment being shown for illustrative purposes to be to jaw 36. Stop 56 prevents a held needle cap 10 from being pushed through jaws 34 and 36 during the needle capping operation (FIG. 8).

As can be seen in FIG. 6, it is preferred that distal longitudinal edge regions of jaws 34 and 36 (that is, distal relative to handle 32) are thinned down to a relatively thin, but not necessarily sharp edge. This enables jaws 34 and 36 to scoop up a needle cap 10 from a surface 58 (FIG. 7) in an easy manner when squeezing pressure on handle 32 is released so as to let the jaws move from their open condition to their closed condition.

It is also preferred, but not necessary, that the distal longitudinal edges of each of jaws 34 and 36 be formed having a plurality of teeth 60 (FIG. 5) the teeth on one jaw interlocking with the teeth on the other jaw when the jaws are in the closed condition (FIG. 4). Teeth 60 further facilitate the scooping up by jaws 34 and 36 of a needle cap 10 form a surface.

Figure 7:
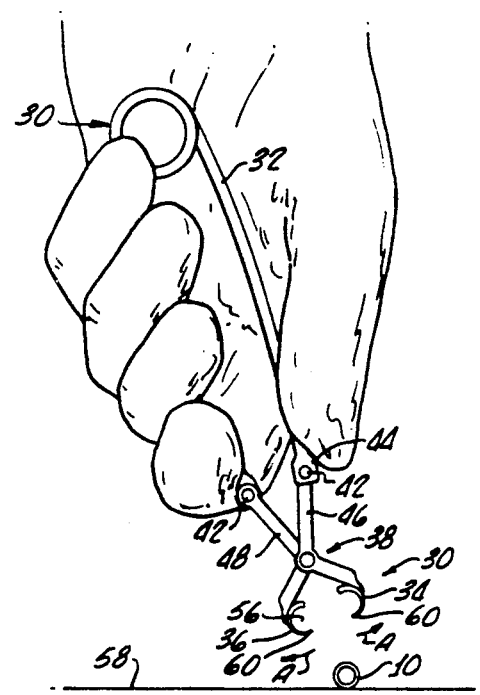
FIG. 7 is a perspective drawing showing the manner in which the cap-holding jaws are caused to be opened by squeezing on the handle of the cap-holding device and showing a needle cap laying on a surface and the manner in which the cap can be picked up by the device.

Because of the configuration of mounting members 46 and 48 and the configuration of handle 32, it can be seen, for example, in FIG. 7, that jaws 34 and 36 are opened widely (in the direction of Arrows "A") with only a relatively small amount of squeezing pressure applied to handle 32 (in the direction of Arrows "B"). This also assists in the easy scooping up, by device 30, of a needle cap 10 resting on surface 58. Mounting members 46 and 48 can be considered to operate as motion multipliers, since they enable jaws 34 and 36 to be opened more widely than would otherwise be the situation for a small amount of squeezing of handle 32.

Spring portion 40 of handle 32 causes jaws 34 and 36 to automatically close when squeezing pressure on the handle is released. As a result, when jaws 34 and 36 are opened widely (by squeezing handle 32) and the jaws are placed downwardly over a needle cap 10, the cap is picked up and held in the jaws merely by easing pressure on the handle In this manner, needle cap 10 can be picked up with one hand (as depicted in FIG. 7) while the other hand, for example, is still holding hypodermic syringe 16. With needle cap 10 held securely away from the user's holding hand 12, the other hand 18 can safely insert needle 14 on syringe 16 into the cap without the risk of sticking the holding hand with the needle (FIG. 8).

Preferably handle 32, members 46 and 48 and jaws 34 and 36, as well as pivot pins 42 and 50 are constructed of a medical grade of metal, such as stainless steel, so that entire device 30 can be sterilized by conventional methods, including autoclaving, without damage to the device.

Although there is described above a specific arrangement of a holder for hypodermic syringe needle caps, especially for holding the caps during needle recapping operations, according to the present invention for illustrating the manner in which the invention may be used to advantage, it will be appreciated that the invention is not limited thereto. Accordingly, any and all variations and modifications that may occur to those skilled in the art are to be considered within the scope and spirit of the appended claims.

What is claimed is:

1. A medical device for holding caps for capping hypodermic syringe needles, said needle cap-holding device comprising:

a. an elongate, manually-operable handle;

b. first and second cap-holding jaws and means for mounting said jaws to said handle so as to cause the jaws to be in a closed condition when the handle is not operated and so as to cause the jaws to open from said closed condition toward an open condition when the handle is operated by a user, said jaws having an inner opening sized to grip a needle cap when the jaws are in the closed condition and having an axial length which is substantially greater than the cross sectional dimension of the jaws when the jaws are in the closed condition, said mounting means mounting the jaws so that a longitudinal axis thereof is substantial perpendicular to the longitudinal axis of the handle and so that the jaws have one pair of longitudinally opposing edges which are distal relative to the handle and another pair of opposing longitudinal edges which are proximal relative to the handle, said pair of distal edges being relatively thin so as to enable the jaws to pick up a needle cap from a surface when the handle is operated to cause the jaws to be in the open condition and when the jaws are returned to the closed condition;

c. biasing means for urging the jaws toward the closed condition when the handle is not operated; and d. stopping means attached to one end region of at least one of the jaws for preventing a held cap from being pushed axially through the jaws during a needle capping operation.

2. The needle cap-holding device as claimed in claim 1, wherein said distal pair of opposing jaw edges are formed having a plurality of teeth which interlock when the jaws are in the closed condition.

3. The needle cap-holding device as claimed in claim 1, wherein the device is constructed from a medical grade of metal.

4. The needle cap-holding device as claimed in claim 3, wherein the metal is stainless steel.

5. The needle cap-holding device as claimed in claim 1, wherein the first and second jaws are similar to one another and are constructed of elongate sections of a tube.

6. A medical device for holding caps for capping hypodermic syringe needles, said needle cap-holding device comprising:

a. an elongate, squeezeable handle;

b. elongate first and second cap-holding jaws and means for mounting said jaws to said handle so as to cause the jaws to be in a closed condition when the handle is not squeezed and so as to cause the jaws to open from said closed condition toward an open condition when the handle is squeezed, said jaws having an inner opening sized to grip a needle cap when the jaws are in the closed condition and having an axial length which is substantially greater than the cross sectional dimension of the jaws when the jaws are in the closed condition, said mounting means mounting the jaws so that a longitudinal axis thereof is substantial perpendicular to the longitudinal axis of the handle and so that the jaws have one pair of longitudinally opposing edges which are distal relative to the handle and another pair of opposing longitudinal edges which are proximal relative to the handle, said pair of distal edges being relatively thin so as to enable the jaws to pick up a needle cap from a surface when the handle is squeezed to cause the jaws to be in the open condition and squeezing pressure on the handle is then released; and stop means, attached to one end region of at least one of the jaws, for preventing a held cap from being pushed axially through the jaws during a needle capping operation.

7. The needle cap-holding device as claimed in claim 6, wherein said jaw mounting means include jaw movement multiplying means configured so that a relatively small amount of squeezing of the handle causes the jaws to open widely.

8. The needle cap-holding device as claimed in claim 6, wherein said distal pair of opposing jaw edges are formed having a plurality of teeth which interlock when the jaws are in the closed condition.

9. The needle cap-holding device as claimed in claim 6, wherein the handle includes spring means for causing the jaws to be retained in the closed condition when the handle is released.

10. The needle cap-holding device as claimed in claim 6, wherein the device is constructed of stainless steel.

11. A medical device for holding caps for capping hypodermic syringe needles, said needle cap-holding device comprising:

a. an elongate, squeezeable handle;

b. elongate first and second cap-holding jaws, each of said jaws being constructed of an elongate half of a tube and means for mounting said jaws to said handle so as to cause the jaws to be in a closed condition when the handle is not squeezed and so as to cause the jaws to open from said closed condition toward an open condition when the handle is squeezed, said jaws having an inner opening sized to grip a needle cap when the jaws are in the closed condition and having an axial length which is substantially greater than the cross sectional dimension of the jaws when the jaws are in the closed condition, said mounting means mounting the jaws so that a longitudinal axis thereof is substantial perpendicular to the longitudinal axis of the handle and so that the jaws have one pair of longitudinally opposing edges which are distal relative to the handle and another pair of opposing longitudinal edges which are proximal relative to the handle, said jaw mounting means including jaw movement multiplying means configured so that when the handle is squeezed a relatively small amount, the jaws are caused to open widely, said pair of distal edges being relatively thin so as to enable the jaws to pick up a needle cap from a surface when the handle is squeezed to cause the jaws to be in the open condition and squeezing pressure on the handle is then released;

c. spring means for urging the jaws toward the closed position when the handle is not squeezed; and d. stop means, attached to one end region of at least one of the jaws, for preventing a held cap from being pushed axially through the jaws during a needle capping operation.

12. The needle cap-holding device as claimed in claim 11, wherein said distal pair of opposing jaw edges are formed having a plurality of teeth which interlock when the jaws are in the closed condition.

13. The needle cap-holding device as claimed in claim 11, wherein the device is constructed of stainless steel.

14. A medical device for holding caps for capping hypodermic syringe needles, said needle cap-holding device comprising:

a. an elongate, squeezeable handle;

b. elongate first and second cap-holding jaws and means for mounting said jaws to said handle so as to cause the jaws to be in a closed condition when the handle is not squeezed and so as to cause the jaws to open from said closed condition toward an open condition when the handle is squeezed, said jaws having an inner diameter sized to grip a needle cap when the jaws are in the closed condition and having an axial length which is substantially greater than the cross sectional diameter of the jaws when the jaws are in the closed condition, said mounting means mounting the jaws so that a longitudinal axis thereof is substantial perpendicular to the longitudinal axis of the handle and so that the jaws have one pair of longitudinally opposing edges which are distal relative to the handle and another pair of opposing longitudinal edges which are proximal relative to the handle, said jaw mounting means including jaw movement multiplying means configured so that when the handle is squeezed a relatively small amount, the jaws are caused to open widely, said pair of distal edges being relatively thin so as to enable the jaws to pick up a needle cap from a surface when the handle is squeezed to cause the jaws to be in the open condition and squeezing pressure on the handle is then released;

c. spring means for urging the jaws toward the closed position when the handle is not squeezed; and d. a stop attached to one end region of at least one of the jaws for preventing a held cap from being pushed axially through the jaws during a needle capping operation.

15. The needle cap-holding device as claimed in claim 14, wherein said distal pair of opposing jaw edges are formed having a plurality of teeth which interlock when the jaws are in the closed condition.

16. The needle cap-holding device as claimed in claim 14, wherein the device is constructed of stainless steel.

17. The needle cap-holding device as claimed in claim 14, wherein the first and second jaws are similar to one another and each of said jaws is constructed of an elongate half of a tube.

* * * * *